(12) United States Patent
Klingenbeck-Regn

(10) Patent No.: US 7,837,385 B2
(45) Date of Patent: Nov. 23, 2010

(54) METHOD FOR RECORDING X-RAY IMAGES BY MEANS OF A ROBOTICALLY CONTROLLED C-ARM SYSTEM AND RECORDING DEVICE FOR RECORDING X-RAY IMAGES

(75) Inventor: Klaus Klingenbeck-Regn, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 75 days.

(21) Appl. No.: 11/890,402

(22) Filed: Aug. 6, 2007

(65) Prior Publication Data
US 2008/0037712 A1    Feb. 14, 2008

(30) Foreign Application Priority Data
Aug. 10, 2006    (DE)    ........................ 10 2006 037 564

(51) Int. Cl.
   *H05G 1/02*    (2006.01)
(52) U.S. Cl. ......................................... 378/197; 378/62
(58) Field of Classification Search ......... 378/195–198, 378/62
See application file for complete search history.

(56) References Cited

U.S. PATENT DOCUMENTS

| | | | | |
|---|---|---|---|---|
| 5,386,453 | A * | 1/1995 | Harrawood et al. | .......... 378/196 |
| 7,338,207 | B2 * | 3/2008 | Gregerson et al. | .......... 378/198 |
| 2001/0036246 | A1 * | 11/2001 | Graumann | .................... 378/39 |
| 2003/0099328 | A1 * | 5/2003 | Jensen et al. | ................. 378/198 |
| 2004/0066906 | A1 * | 4/2004 | Hornegger et al. | .......... 378/197 |

FOREIGN PATENT DOCUMENTS

| | | |
|---|---|---|
| DE | 10153787 B4 | 5/2003 |
| DE | 10241184 A1 | 4/2004 |

(Continued)

OTHER PUBLICATIONS

Defrise, M. et al., "Enlargement of the region of accurate reconstruction in computed tomography from truncated data", The 8th international meeting on fully three-dimensional image reconstruction in radiology and nuclear medicine, 2005, p. 46-50.
Arai, I. et al., "A New Class of Super-Short-Scan Algorithms for Fan-Beam Reconstruction", IEEE Nuclear Science Symposium Conference Record, 2005, vol. 4, p. 2296-2300.

(Continued)

*Primary Examiner*—Hoon Song

(57) ABSTRACT

The present invention relates to a method and a device for recording X-ray images by means of a robotically controlled C-arm system which includes an image recording system (9, 10) that can be rotated in a recording plane around a turning center (17) by means of a C-arm (7) and with which, through rotating of the C-arm (7), a plurality of radioscopic images of a region (14) of interest in an object (13) positioned on an object positioning facility (15) are recorded at different rotation angles, from which images one or more cross-sectional images or a three-dimensional image of a region (14) in the object can be reconstructed. With the method, the C-arm (7) is compliantly repositioned in a collision-free manner in synchronism with the rotation such that the region (14) of interest in an object will, at least at each rotation angle at which image recording takes place, be located within a cone beam (16) of an X-ray bundle of the image recording system (9, 10). The method and associated robotically controlled recording device thus enable the three-dimensional image reconstruction also of regions located at the edge of the object's longitudinal center line.

8 Claims, 2 Drawing Sheets

FOREIGN PATENT DOCUMENTS

| DE | 10 2004 062 473 A1 | 4/2006 |
| --- | --- | --- |
| DE | 202005021106 U1 | 4/2007 |
| EP | 1127549 A2 | 8/2001 |

OTHER PUBLICATIONS

Feldkamp, I.A. et al., "Practical cone-beam algorithm", J. Opt. Soc. Am. A, vol. 1, Jun. 1984, p. 612-619.

* cited by examiner

METHOD FOR RECORDING X-RAY IMAGES BY MEANS OF A ROBOTICALLY CONTROLLED C-ARM SYSTEM AND RECORDING DEVICE FOR RECORDING X-RAY IMAGES

The present invention relates to a method for recording X-ray images by means of a robotically controlled C-arm system which includes an image recording system that can be rotated in a recording plane around a turning center by means of a C-arm and with which, through rotating of the C-arm, a plurality of radioscopic images of a region of interest in an object positioned on an object positioning facility are recorded at different rotation angles, from which images one or more cross-sectional images or a three-dimensional image of the region of interest in the object can be reconstructed. The invention relates further to a robotically controlled recording device embodied for implementing the proposed method.

C-arm systems are widely used in medical practice. In systems of said type the X-ray detector and X-ray source are attached opposite each other to what is termed a C-arm embodied for executing a rotational movement. The image recording system with the X-ray source and X-ray detector can thereby be rotated around a turning center, what is termed the isocenter of the C-arm system. Not only two-dimensional radioscopic images can be obtained in this way using said modern C-arm systems but, through the image recording system's being rotated around the patient, also three-dimensional, CT-like images or cross-sectional images. From the radioscopic images recorded at different rotation angles the three-dimensional or cross-sectional images are reconstructed in a similar way as in the case of a computer tomograph (CT). It is thereby possible to three-dimensionally visualize soft parts or, by subtracting contrast media images and native images, angiographies.

Also known alongside said widespread C-arm systems are robotically controlled C-arm systems where a C-arm with an X-ray source and an X-ray detector located opposite the X-ray source is coupled to the hand of a robot which moves said X-ray recording system around the object of interest for the purpose of recording the two-dimensional X-ray images.

The region being X-rayed in the object of which region a three-dimensional image is subsequently obtained through reconstruction is delimited by the size of the cone beam of the X-ray bundle. The size of the cone beam is in turn matched to the size and distance of the X-ray detector, as a rule a flat detector. The region of interest in the object, what is termed the VOI (Volume of Interest), must be located in the C-arm system's isocenter so it can be imaged by the image recording system at every rotation angle or, as the case may be, projection angle. That condition is readily met in the case of regions of interest in an object in medical imaging that are located centrally along a patient's longitudinal center line such as, for instance, the head, heart, or central abdominal cavity. If, however, regions at the edge of the patient's longitudinal center line are to be displayed, such as, for instance, the liver or kidneys, then the above condition will give rise to problems. Said regions can only be moved in a limited manner into the isocenter of the C-arm system because severe restrictions apply to moving the patient or, as the case may be, patient positioning table laterally through the rotating C-arm with the image recording system attached thereto.

If the region of interest, for example an organ, cannot be completely positioned within the cone beam of the X-ray bundle, then it will not be possible to exactly reconstruct the organ from the X-ray images recorded at a plurality of rotation angles.

The publication DE 102004062473 A1 discloses a medical radiotherapy arrangement employing a robotically controlled C-arm system, which arrangement has a patient positioning facility with a patient table that can be moved in front of an exit window for a stationary particle beam in a suitable irradiating position for irradiating a patient. Further provided is an X-ray diagnostic device for determining or verifying the location of a tumor requiring to be irradiated, with the X-ray diagnostic device having an X-ray source and a detector both of which can be moved within the space around the patient table located in the irradiating position. The possibility is provided thereby of already verifying the tumor's location in the irradiating position so that the patient will not have to be moved.

The object of the present invention is to disclose a method and a robotically controlled recording device by means of both of which three-dimensional imaging of an object's lateral edge regions is also enabled.

Said object is achieved by means of the method and the recording device according to claims 1 and 5. Advantageous embodiments of the method and of the robotically controlled recording device are the subject matter of the dependent claims or can be derived from the following description and the exemplary embodiment.

With the proposed method for recording X-ray images by means of a robotically controlled C-arm system which includes an image recording system that can be rotated in a recording plane around a turning center by means of a C-arm, a plurality of radioscopic images of a region of interest in an object positioned on an object positioning facility are recorded in a known manner at different rotation angles by rotation of the C-arm, from which images one of more cross-sectional images or a three-dimensional image of a region in the object can then be reconstructed. The method is characterized in that the C-arm system's C-arm is compliantly repositioned in a collision-free manner in synchronism with the rotation such that the region of interest in an object will, at least at each rotation angle at which image recording takes place, be located within a cone beam of the X-ray bundle of the image recording system.

The present method thus exploits the fact that whereas the C-arm can indeed be displaced laterally only slightly when in a lateral position in the case of a robotically controlled C-arm system, at other rotation angles the C-arm can be displaced or, as the case may be, compliantly repositioned laterally over much greater distances in a collision-free manner. What is achieved through the proposed compliant repositioning of the C-arm within the collision-free space in synchronism with the rotation of the C-arm or, as the case may be, image recording system is that the region of interest will be located within the cone beam of the X-ray bundle each time a radioscopic image is recorded. The central beam of the X-ray bundle directed by the X-ray tube onto the X-ray detector will thus at said rotation angles always largely pass through the region of interest so that said region will be imaged completely. That is the prerequisite for correctly reconstructing one or more cross-sectional images or a three-dimensional image of said region from the recorded radioscopic images.

The robotically controlled displacement of the C-arm corresponds to a displacement of the image recording system's turning center, which displacement is enabled by compliant repositioning of the C-arm by means of the robot. In the case of a robotically controlled C-arm system the turning center can be displaced variably within the space within the robotic arm's range (working space of the robotic arm). The region of interest, for example an organ, can always be kept within the X-ray beam cone through the turning center's being displaced during the rotation that takes place while images are being recorded. That enables the region of interest to be accurately reconstructed from the X-ray image data recorded at different rotation angles. The displacement must in this case take place in synchronism with the rotational movement in order to reliably avoid collisions during rotation between the image recording system and the object or object positioning facility.

The initial position of the respective region of interest relative to the C-arm system's initial turning center can therein be input to the robotically controlled C-arm system's control device by, for example, the user as a lateral distance. It is, of course, also possible first to obtain one or more overview recordings of the object with no compliant repositioning movement and display them to the user on an image display device, with the user's then being able to mark the region of interest therein. The initial distance between the region of interest and the initial turning center can in that way also be determined automatically by an image computer of the C-arm system. The maximum collision-free lateral displacement of the C-arm at its various rotation angles must be determined in advance for the respective C-arm system. The synchronizing of the image recording system's or, as the case may be, C-arm's rotation with the compliant repositioning of the C-arm will not therein pose any problems because the C-arm's momentary rotation angle in each case will be known to the system having hitherto also had to be registered for each image recording for subsequently reconstructing three-dimensional images.

In an advantageous development of the method, alongside the compliant repositioning of the C-arm or, as the case may be, turning center, the distance between the detector and X-ray source on the C-arm is also varied to enable collision-free rotation during image recording. Said distance can be adjusted in the case of robotically controlled C-arms which as a rule have a U-shaped instead of a C-shaped support for the image recording system. The term C-arm must therefore in the present patent application be understood as also including U-shaped, V-shaped, or similar supports of said type in the case of which the X-ray tube and X-ray detector are secured to two limbs located opposite each other. This varying of the distance between the X-ray source and X-ray detector also takes place in synchronism with the C-arm's rotational movement.

The proposed robotically controlled recording device for recording X-ray images thus includes in a known manner a robotically controlled C-arm system having an image recording system that can be rotated in a recording plane around a turning center, an object positioning facility on which an object requiring to be examined can be positioned in the C-arm's turning center, and a control device for controlling the C-arm's rotation and for controlling the image recording system for recording radioscopic images at different rotation angles. The robot is a robot having a plurality of axes of motion that can be controlled via the control device for moving a robotic hand. The recording device that is the subject matter of the present invention is characterized in that the control device controls the C-arm in synchronism with the C-arm's rotation in such a way for performing a collision-free compliant repositioning movement that the region of interest in an object will, at least at each rotation angle at which image recording takes place, be located within a cone beam of the X-ray bundle of the image recording system.

The robot in the proposed robotically controlled C-arm system can have, for example, six rotational axes. It can therein in an embodiment be a kink-arm robot of the kind employed on assembly lines in the automobile industry.

Since owing to the compliant repositioning movement, or in combination with a change in the distance between the X-ray source and X-ray detector, both the position of the momentary turning center and the distance of the focus detector can change while the image recording system is revolving, the known reconstruction algorithms have to be appropriately adjusted for a three-dimensional reconstruction of the region of interest. Suitable account can accordingly be taken of said variable geometry if back-projection is used in accordance with what is termed the Feldkamp method (see L. A. Feldkamp et al., "Practical Cone-Beam Algorithm", J. Opt. Soc. Am. A1 (1984), pages 612 to 619).

Since the geometric relationships between the X-ray source, object positioning facility, and X-ray detector are known before any X-ray images are recorded, there can be an initial rough prospective estimation of the requisite focal and detector path. On the basis of a few radioscopic recordings obtained from different directions, the patient's geometry can be estimated in such a way that the focal and detector path can be individually matched to the respective object positioned on the object positioning facility. Having been determined once, the scanning path can also be used for multiple revolutions because although the position of internal organs such as, for example, the liver or heart can change, the patient's external contours will remain largely unchanged while X-ray images are being recorded.

An additional advantage of the present method and associated recording device is that the drawbacks of what are termed truncated projections are therein avoided. Said truncated projections will occur when the X-ray bundle fails to completely register the region of interest in individual projections, meaning when the region of interest projects beyond the X-ray bundle's cone beam. Accurate reconstructing of the region of interest will then no longer be possible. If, though, as is made possible by the present method, a part of the edge of the patient is contained within the VOI, then the part of the VOI that can be linked to the edge by line segments can be reconstructed exactly, with its being necessary for said line segments to be contained completely within the VOI. Relevant details can be found in M. Defrise et al., "Enlargement of the Region of Accurate Reconstruction in Computed Tomography from Truncated Data", Proceedings of the Int. Meeting on Fully Three-Dimensional Image Reconstruction in Radiology and Nuclear Medicine, Salt Lake City, Utah, USA, Jul. 6 to 9, 2005, pages 46 to 50, or in I. Arai et al., "A New Class of Super-Short-Scan Algorithms for Fan Beam Reconstruction", IEEE Nuclear Science Symposium Conference Record, Fajardo, Puerto Rico, Oct. 23-29, 2005.

The present method and associated recording device will be explained again below with reference to an exemplary embodiment in conjunction with the drawings, in which.

Figure 1:
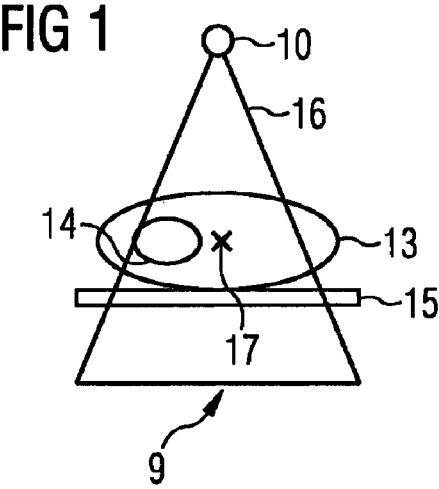
FIG. 1 is a schematic of a recording situation in which the region of interest is located just within the X-ray beam cone.

In known robotically controlled C-arm systems the C-arm and image recording system located thereon are rotated under robotic control around a stationary turning center in which an object requiring to be examined is positioned on an object positioning facility, as a rule a patient table. FIG. 1 shows in a highly schematic form a recording situation of said kind with a patient 13 positioned on the patient table 15. In this example, owing to the geometric conditions, the patient is not located completely within the X-ray beam cone 16 emanating from the image recording system's X-ray source 1, which beam cone will, after traversing the patient, strike the X-ray detector 9 located opposite. The image recording system consisting of the X-ray source 1 and X-ray detector 9 will rotate around the turning center 17 during image recording in order to obtain X-ray recordings of the patient at different rotation angles. Because the patient 13 is projecting laterally beyond the X-ray beam cone 16 it is necessary to correct truncating of the projections during three-dimensional image reconstruction. Said corrections are known as truncation corrections. Because the region 14 of interest, for example an organ such as the liver, will, however, in that example be located within the X-ray beam cone 16 at all rotation angles, said organ will still be accurately imaged when the X-ray images are recorded.

Figure 2:
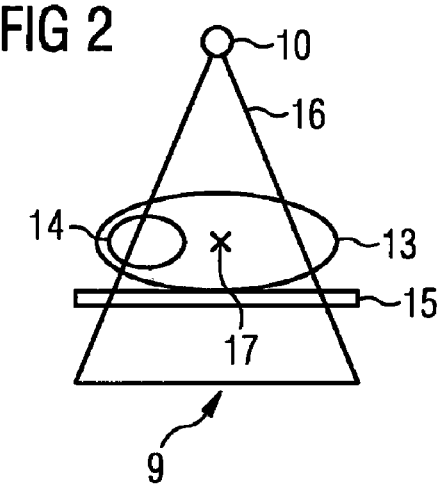
FIG. 2 is a schematic of a recording situation in which the region of interest projects beyond the X-ray beam cone.
Figure 3:
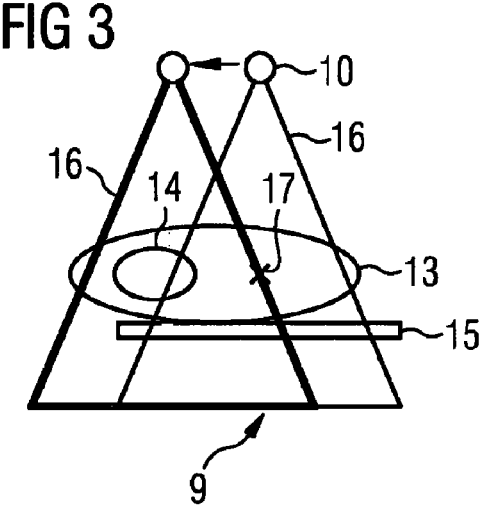
FIG. 3 is a schematic of a recording situation in which the region of interest is again located within the X-ray beam cone through compliant repositioning of the C-arm.

If, however, the region 14 of interest itself is not, as indicated in FIG. 2, located throughout the rotation completely within the beam cone 16, then it will subsequently no longer be possible to accurately reconstruct the region of interest from the recorded radioscopic images. With the present method the robotically controlled C-arm will in that case be variably displaced within the space in such a way that the region 14 of interest will still be located within the beam cone 16 at every rotation angle. That is readily possible by suitably controlling the robot compliantly repositioning the C-arm within the robot's range of movement. FIG. 3 shows such lateral displacing of the C-arm or, as the case may be, the image recording system secured thereto, so that the region of interest will again be located within the momentary turning center.

Figure 4:
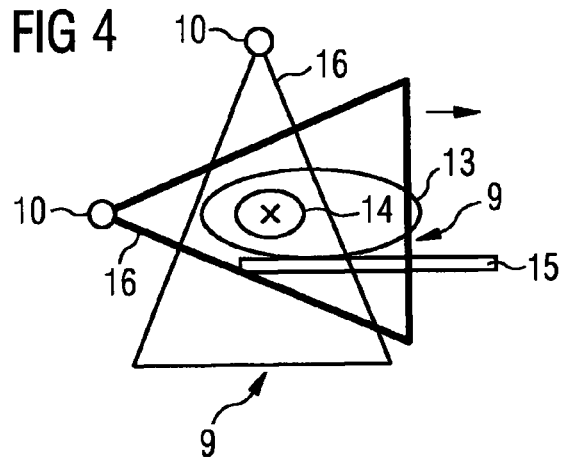
FIG. 4 is a schematic indicating collision-free compliant repositioning of the C-arm according to the present invention.

The lateral displacement shown in the example in FIG. 3 can, though, give rise to collision problems because if said displacement is maintained at certain rotation angles a collision may occur between the X-ray detector or X-ray tube and patient table, especially in the lateral projection direction. That is why with the present method the C-arm is compliantly repositioned variably, thereby insuring that the entire rotational movement will be free from collisions. That is indicated by way of example in FIG. 4, where the C-arm in a vertical projection is displaced laterally in such a way that the momentary turning center is located in the region of interest, although said lateral displacement will in a lateral projection be largely rescinded in order to avoid a collision between the X-ray detector and object or, as the case may be, patient table. Said last-cited displacement in the opposite direction is indicated by an arrow. It can also be seen in the figure that the region 14 of interest will, in a lateral projection, nonetheless still be located within the X-ray beam cone 16 thanks to a displacement of said type.

With the present method the C-arm is thus compliantly repositioned variably in such a way depending on the momentary rotation angle that the region 14 of interest will always be located within the X-ray beam cone 16 and collisions will at the same time be avoided. The distance between the X-ray source and X-ray detector can additionally also be increased at rotation angles at which there is a higher risk of collision.

Thus in the case of the present method and associated recording device the different spatial relationships are used as they arise in the C-arm's various rotational positions. While the C-arm's lateral displacement potential is highly limited in the image recording system's lateral position in order to avoid collisions, virtually any lateral displacement of the C-arm is possible in the vertical position without the risk of collisions. In intermediate positions it will still be possible without impeding rotation to execute a correspondingly smaller lateral displacement that is larger than the displacement potential in the case of a lateral projection. The C-arm is thus laterally displaced as a function of the momentary rotation angle in synchronism with the rotational movement in order to always keep the region 14 of interest within the X-ray beam cone 16. That can be done via the robot's control in the case of a robotically controlled C-arm system.

Figure 5:
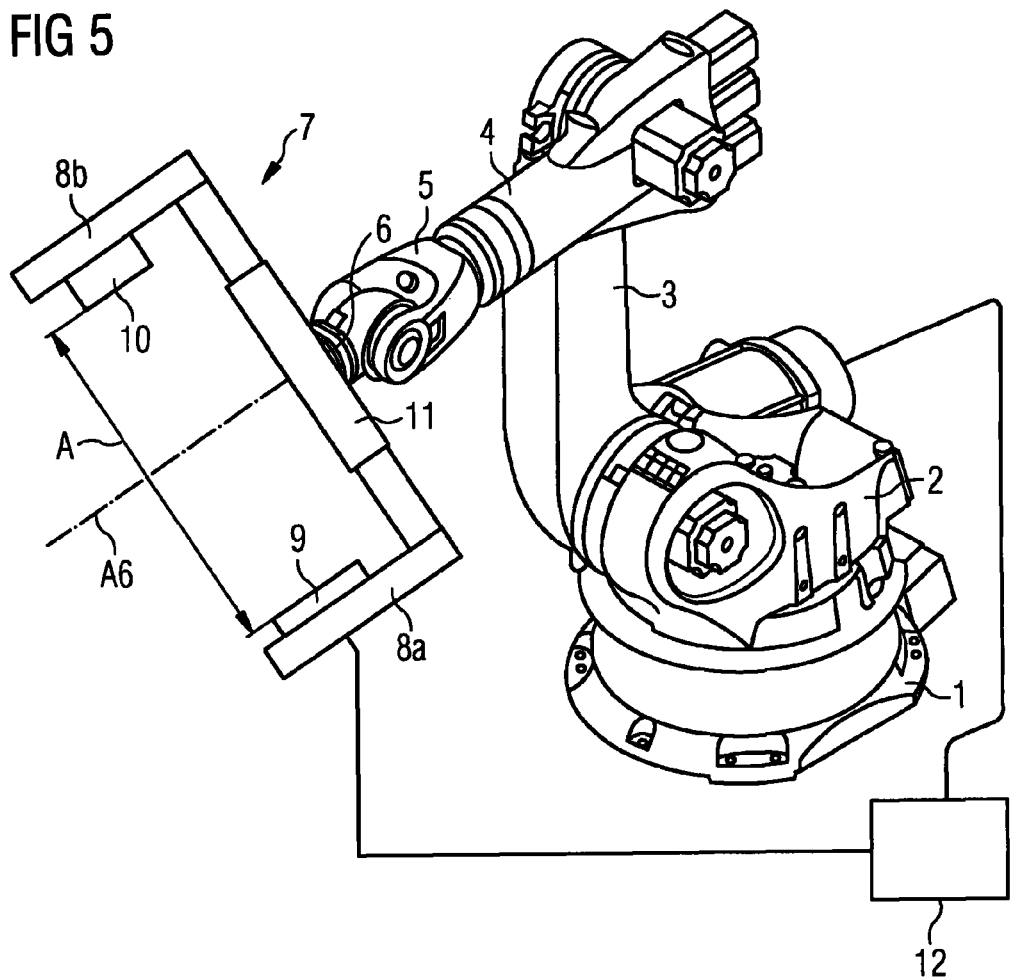
FIG. 5 is a perspective view of an inventive recording device.

FIG. 5 is a perspective view of an exemplary robotically controlled C-arm system of said type. Said system includes a known robot having six rotational axes. Attached rotatably around a first rotational axis to a base stand 1, that can be permanently mounted on the floor of an operating theater, for example, is a carousel 2. Attached tiltably around a second rotational axis to the carousel 2 is a swinging bracket 3. Secured rotatably around a third rotational axis to the swinging bracket 3 is an arm 4. Attached rotatably around a fourth rotational axis to the end of the arm 4 is a robotic hand 5. The hand 5 has an interface 6 for coupling a tool which via the interface 6 is rotatable around a rotational axis and tiltable around a fifth rotational axis running perpendicular thereto. Coupled to the interface 6 of the hand 5 is a support referenced generally by the reference numeral 7.

The support 7 is in the present example embodied in the manner of a U profile having two limbs 8a, 8b located opposite each other. Attached opposite each other to the first limb 8a is an X-ray detector 9 and to the second limb 8b an X-ray source 10. The first 8a and the second limb 8b can be attached in a linearly moveable manner with reference to a central element 11 of the support so that the distance A between the X-ray detector 9 and X-ray source 10 can be adjusted. In an embodiment of the present recording device, said distance can be adjusted in a motorized manner.

For rotationally moving the image recording system formed from the X-ray source 10 and X-ray detector 9 around the rotational axis A6 the robot is driven via the control device 12, which also undertakes image recording by means of the image recording system and, where applicable, motorized adjusting of the distance A between the X-ray source 10 and X-ray detector 9. The control device 12 drives the robot in keeping with the above-described method for image recording and for compliantly repositioning the C-arm and, where applicable, compliantly adjusting the distance A.

The invention claimed is:

1. A method for recording X-ray images of a region of interest in an object by an image recording system attached to a C-arm, comprising:
   rotating the C-arm about a center of rotation;
   recording the x-ray images at a plurality of angles of rotation while rotating the C-arm;
   rescinding a lateral displacement of the C-arm when the C-arm is in a lateral position; and
   synchronously horizontally moving the C-arm with the rotation so that the region of interest lies within a cone beam of an X-ray bundle of the image recording system at the angles of rotation.

2. The method as claimed in claim 1, wherein a distance between an X-ray source and an X-ray detector of the image recording system is synchronously adjusted with the rotation to avoid a collision of the C-arm with the object or an object positioning device.

3. The method as claimed in claim 1, wherein the C-arm is a robotically controlled C-arm.

4. The method as claimed in claim 1, furthering comprising determining a maximum collision-free lateral displacement of the C-arm at the angles of rotation.

5. A recording device for recording X-ray images of a region of interest in an object, comprising:
- an image recording system that rotates about a center of rotation and records the x-ray images of the region of interest at a plurality of angles of rotation;
- a C-arm that rotates the image recording system and is synchronously horizontally moved with the rotation so that the region of interest lies within a cone beam of an X-ray bundle of the image recording system at the angles of rotation; and
- a control device that controls the rotation of the C-arm and the recording of the X-ray images and synchronously controls the horizontal move of the C-arm with the rotation so that a lateral displacement of the C-arm is rescinded when the C-arm is in a lateral position.

6. The recording device as claimed in claim 5, wherein a distance between an X-ray source and an X-ray detector of the image recording system is synchronously adjusted with the rotation to avoid a collision of the C-arm with the object or an object positioning device.

7. The recording device as claimed in claim 6, wherein the distance is motorized adjusted.

8. The recording device as claimed in claim 5, wherein the C-arm is a robotically controlled C-arm.

* * * * *